(12) United States Patent
Fouda et al.

(10) Patent No.: US 9,562,151 B2
(45) Date of Patent: Feb. 7, 2017

(54) COMPOSITION COMPRISING NANOPARTICLES AND A METHOD FOR THE PREPARATION THEREOF

(71) Applicant: King Saud University, Riyadh (SA)

(72) Inventors: Moustafa Mohamed Gaballa El-Sayed Fouda, Riyadh (SA); Mehrez El-Sayed El-Naggar, Riyadh (SA); Tharwat Ibrahim Shaheen, Riyadh (SA); Salem S. Al Deyab, Riyadh (SA)

(73) Assignee: King Saud University, Riyadh (SA)

( * ) Notice: Subject to any disclaimer, the term of this patent is extended or adjusted under 35 U.S.C. 154(b) by 298 days.

(21) Appl. No.: 13/692,052

(22) Filed: Dec. 3, 2012

(65) Prior Publication Data

US 2013/0152823 A1  Jun. 20, 2013

(30) Foreign Application Priority Data

Dec. 14, 2011 (EP) .................................. 11193467

(51) Int. Cl.
| | | |
|---|---|---|
| *C08L 3/02* | (2006.01) |
| *B22F 1/00* | (2006.01) |
| *B22F 9/24* | (2006.01) |
| *A61K 33/38* | (2006.01) |
| *C22C 5/06* | (2006.01) |
| *A61K 33/24* | (2006.01) |
| *A61K 33/26* | (2006.01) |
| *A61K 33/30* | (2006.01) |
| *A61K 33/34* | (2006.01) |

(Continued)

(52) U.S. Cl.
CPC ................ *C08L 3/02* (2013.01); *A01N 59/16* (2013.01); *A01N 59/20* (2013.01); *A61K 9/5161* (2013.01); *A61K 33/24* (2013.01); *A61K 33/26* (2013.01); *A61K 33/30* (2013.01); *A61K 33/34* (2013.01); *A61K 33/38* (2013.01); *B22F 1/0022* (2013.01); *B22F 1/0059* (2013.01); *B22F 9/24* (2013.01); *B82Y 30/00* (2013.01); *C22C 5/06* (2013.01); *B22F 1/0014* (2013.01); *B22F 1/0018* (2013.01)

(58) Field of Classification Search
None
See application file for complete search history.

(56) References Cited

U.S. PATENT DOCUMENTS 5,095,054 A * 3/1992 Lay ........................ A01N 25/10
264/328.14
2006/0045916 A1  3/2006 Raghuraman et al.
(Continued)

FOREIGN PATENT DOCUMENTS

WO  2009/131603  10/2009

OTHER PUBLICATIONS

P. Vasileva et al: "Synthesis of starch-stabilized silver nanoparticles and their application as a surface plasmon resonance-based sensor of hydrogen peroxide", Colloids and Surfaces A: Physicochemical and Engineering Aspects, vol. 382, No. 1-3, Jun. 1, 2011, pp. 203-210.

(Continued)

*Primary Examiner* — Colin W Slifka
(74) *Attorney, Agent, or Firm* — Renner, Otto, Boisselle & Sklar, LLP (57) ABSTRACT

The present invention relates to a composition comprising nanoparticles stabilized by an at least partially deprotonated biopolymer and a method for the preparation thereof.

4 Claims, 6 Drawing Sheets

(51) Int. Cl.
*A61K 9/51*     (2006.01)
*A01N 59/16*    (2006.01)
*A01N 59/20*    (2006.01)
*B82Y 30/00*    (2011.01)

(56) References Cited

U.S. PATENT DOCUMENTS

2006/0148943 A1* 7/2006 Mikkonen ............ C08K 5/1539
                                              524/112
2009/0266202 A1 10/2009 Tai et al.
2011/0064825 A1  3/2011 Goia et al.
2013/0023714 A1* 1/2013 Johnston .............. A61K 9/0009
                                              600/1

OTHER PUBLICATIONS

Singh M. et al: "Role of pH in the green synthesis of silver nanoparticles", Materials Letters, vol. 63, No. 3-4, Feb. 15, 2009, pp. 425-427.
El-Rafie M. H. et al: "Environmental synthesis of silver nanoparticles using hydroxypropyl starch and their characterization", Carbohydrate Polymers, vol. 86, No. 2, Apr. 30, 2011, pp. 630-635.
Zameer Shervani et al: "Carbohydrate-directed synthesis of silver and gold nanoparticles: effect of the structure of carbohydrates and reducing agents on the size and morphology of the composites", Carbohydrate Research, vol. 346, No. 5, Jan. 19, 2011, pp. 651-658.
EP11193467.5; European Search Report dated Sep. 18, 2012.

* cited by examiner

COMPOSITION COMPRISING NANOPARTICLES AND A METHOD FOR THE PREPARATION THEREOF

TECHNICAL FIELD

The present invention relates to a composition comprising nanoparticles and a method for the preparation thereof.

BACKGROUND

Nanotechnology, in particular synthesis and use of nanoparticles, is introduced in many fields and features a plurality of possible applications such as chemical or biological detectors, drug delivery systems, new generation of laser, reinforced materials, thermal barriers and ink jet systems as well as textiles.

Most of the known synthetic methods for the production of silver nanoparticles rely on the use of organic solvents, such as acetone, chloroform, DMSO, etc., and toxic reducing agents, such as hydrazine, DMF, sodium borohydride, etc., in addition to separate stabilizing agents. All previous chemicals are toxic and pose potential environmental and biological risks. Besides this, said substances cause high costs and are therefore not favorable for an industrial application.

Vigneshwaran et al., Carbohydrate research, 2006, 341, 2012-2028, relates to the "green" synthesis of stable silver nanoparticles using soluble starch. It is disclosed that the preparation was carried out in an autoclave at 15 psi at 121° C. for 5 minutes. The nanoparticles obtained this way were found to be stable in aqueous solution over a period of 3 months at room temperature. Soluble starch in terms of this disclosure means linear amylose which was obtained from native starch by separation from the insoluble part (branched amylopectin). The disclosed nanoparticle solutions featured a low concentration of only 50 ppm of silver nanoparticles.

US 2010/0172997 A1 relates to gold, silver and copper nanoparticles stabilized in biocompatible aqueous media. It is disclosed that the nanoparticles can be prepared by photo reduction and thermolysis. Biopolymers such as chitosan, PVA, HPC, PEG, algenic acid etc. were used as stabilizing agents.

US 2007/0269880 A1 relates to a stabilizing solution for submicronic particles. In particular, the synthesis of silver and gold nanoparticles using bitter gourd extract is disclosed. The particles prepared this way feature diameters in a range from 20 to 150 nm. Moreover, a broadening in size distribution of the formed particles was observed.

US 2006/0045916 A1 relates to a method for preparing silver nanoparticles by the reduction of silver ions using phosphine amino acids. The particles are stabilized by a starch previously dissolved in water at a temperature of 100° C.

It is an object of the present invention to provide well stabilized, highly concentrated compositions comprising nanoparticles having a narrow size distribution which can be prepared at low costs under ambient conditions.

SUMMARY

This object is achieved by a composition comprising nanoparticles stabilized by an at least partially deprotonated biopolymer.

Preferably, the nanoparticles are metal and/or metal oxide nanoparticles, preferably Au, Ag, Pd, Pt, Rh, Ir, Cu, Co, Ni, Fe oxides and/or ZnO nanoparticles, more preferably Ag nanoparticles.

More preferably, the biopolymer is starch.

It is preferred that the diameter of the nanoparticles is in a range from 1 to 25 nm, more preferably 4 to 20 nm.

Most preferred, the metal and/or metal oxide concentration is in a range from 100 ppm to 2000 ppm.

Even preferred the nanoparticles feature a narrow size distribution.

The object is further achieved by a method for preparing the inventive composition comprising the steps: a) providing a solution of a base in a first solvent; b) dissolving the biopolymer in the solution of step a); c) optionally diluting the solution obtained in step b) to obtain a first solution; d) optionally adjusting the pH of the solution of step b) or c) to a value higher than 9 to achieve a first solution; e) providing a second solution comprising a nanoparticle precursor in a second solvent; f) adding the second solution to the first solution; g) heating the mixture obtained in step f); and h) optionally at least partially removing first and second solvents.

Preferably, the base is an alkali and/or an alkaline earth hydroxide and/or an alkali and/or an alkaline earth alkoxide, preferably sodium hydroxide, potassium hydroxide, sodium ethanolate and/or sodium n-butylate, most preferably sodium hydroxide and/or potassium hydroxide.

In another preferred embodiment, the first and the second solvent are at least one polar and protic solvent, preferably ethanol and/or water, most preferably water.

Even preferably, steps a), b), c) and/or e) are carried out at 20-30° C.

In a preferred embodiment, the pH of the first solution after step d) is in a range from 10 to 13, preferably 11 to 12, most preferably about 11.5.

Furthermore, it is preferred that the nanoparticle precursor is a metal salt, preferably a metal halogenate, nitrate, sulfate, acetylacetonate, acetate, most preferably metal nitrate.

Further preferred, adding in step f) is carried out dropwise under stirring.

Preferably, the mixture in step g) is heated to a temperature in a range from 40 to 100° C., preferably in a range from 50 to 80° C., more preferably about 60° C.

Finally, it is preferred that heating in step g) is carried out for 10 to 300 min, preferably 20 to 120 min, most preferably for 30 to 60 min.

In a further preferred embodiment, the method comprises the additional step of at least partly removing the first and second solvents, which can be easily done by evaporation and heating.

It was surprisingly found by the inventors that the inventive nanoparticles can be prepared under ambient conditions by using an at least partially deprotonated biopolymer as both a stabilizing and a reduction agent. Especially, organic solvents and/or toxic reducing agents can be avoided, so that potential environmental and biological risks can be prevented. Additionally, the inventive composition can be prepared in a very cost-effective manner and is therefore attractive for industrial applications.

It was further surprisingly found that the inventive composition features an extraordinary long-term stability.

Finally, it was surprisingly found that the inventive method allows the preparation of nanoparticles with a well controlled size and a narrow size distribution.

The composition of the present invention can be advantageously utilized in healthcare, medicinal and industrial antimicrobial applications, such as agents for promoting healing of wounds and reducing information associated with burns.

Starch in terms of the present invention means natural starch consisting of both the linear amylose and the branched amylopectin, wherein the amount of amylopectin is in a range of about 70 to 80%.

Ambient conditions in terms of the present invention mean room temperature (a temperature of about 25° C.) and normal atmospheric pressure (approximately 1013 hPa).

"Narrow size distribution" in terms of the present invention means that according to TEM analysis 95% of the particle sizes lie within a characteristic range corresponding to the respective concentration. For example, in the case of the nanoparticle solution having a concentration of 100 ppm 95% of the particle sizes lie within the range of 4-8 nm and the remaining 5% does not exceed 15 nm reflecting the narrow size distribution of these particles.

The term "nanoparticle precursor" has to be understood as any compound suitable for preparing nanoparticles under the mentioned conditions. For example, besides the mentioned salts which can be reduced to the corresponding metal, easy decomposable zerovalent metal compounds are conceivable.

Data referring to the concentration of the inventive composition are related to the concentration of the nanoparticles in the finally obtained solution.

BRIEF DESCRIPTION OF THE DRAWINGS

Additional advantages and features of the composition and the method of the present invention can be taken from the following detailed description of preferred embodiments with reference to the accompanying figures wherein.

The respective analyses were performed by using the following equipment: UV-vis spectra (PerkinElmer, LAMBDA, 35, USA) from 300 to 600 nm, Transmission Electron Microscope; TEM (JEOL-JEM-1230, Japan), EDX (SEM, JEOL-JSM 5800, Japan).

DETAILED DESCRIPTION

Example 1

Preparation of Sodium Starchate (First Solution)

0.2 g sodium hydroxide was dissolved in a small amount of distilled water (around 5 ml). 1 g of rice starch was added gradually to the sodium hydroxide solution under stirring within 5 minutes. Complete the solution to 100 ml with distilled water till complete solubilization of starch. The resulting sodium starchate solution was heated to 60° C. and the pH of the solution was adjusted to 11.5 by using a 10 M aqueous solution of sodium hydroxide.

Example 2

Preparation of Silver Nitrate Solution (Second Solution)

1.56 g silver nitrate were dissolved in 100 ml distilled water.

Example 3

Preparation of Silver Nanoparticles (100 ppm)

Figure 1:
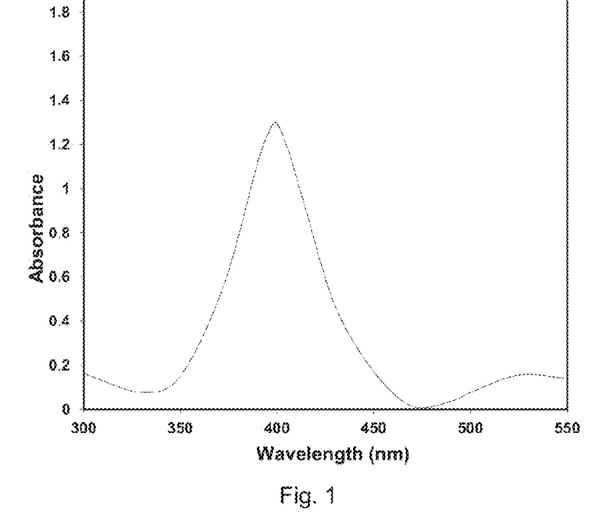
FIG. 1 is a UV-Vis absorption spectrum of silver nanoparticles (100 ppm) prepared at 60° C. and a pH of 11.5 for 30 minutes.
Figure 2:
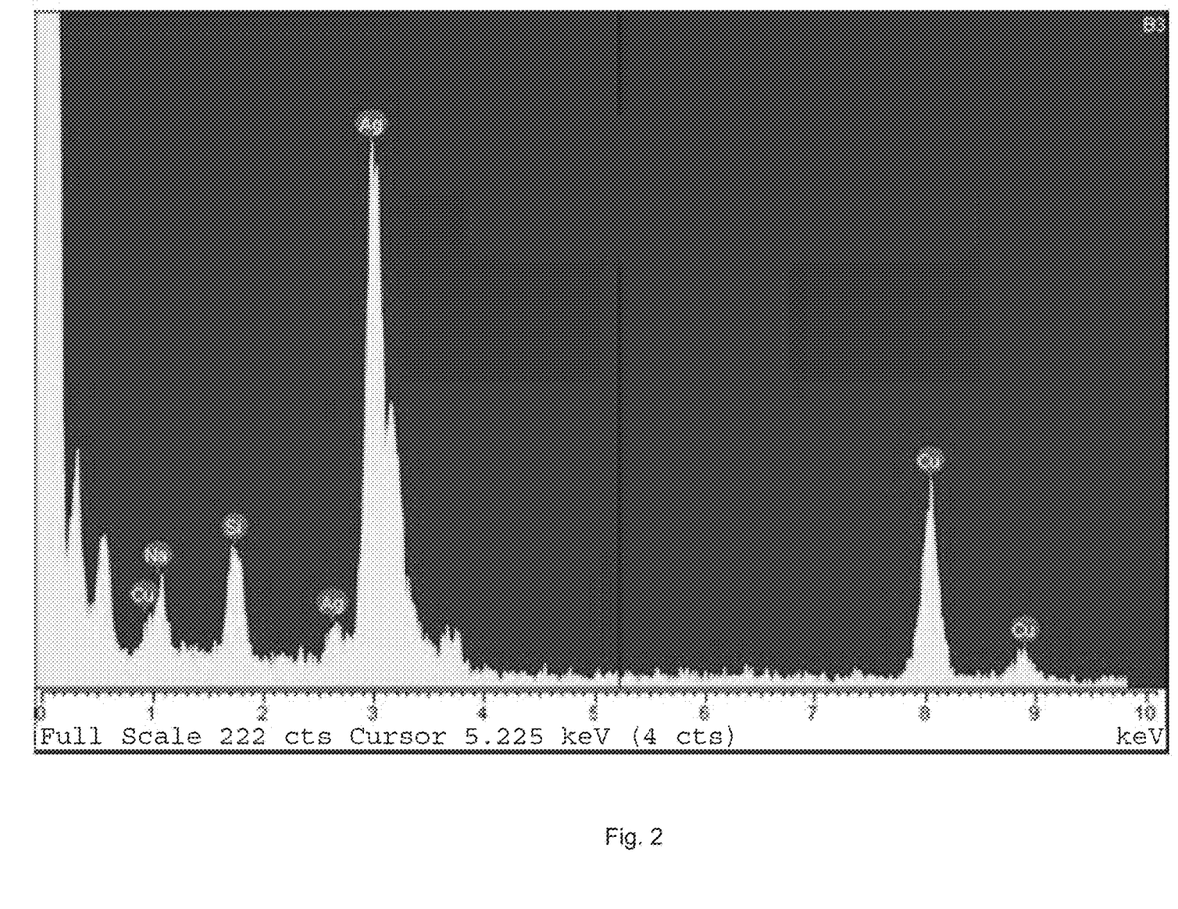
FIG. 2 is an Energy-Dispersive X-ray (EDX) spectrum of silver nanoparticles (100 ppm) prepared at 60° C. and a pH of 11.5 for 30 minutes.
Figure 3:
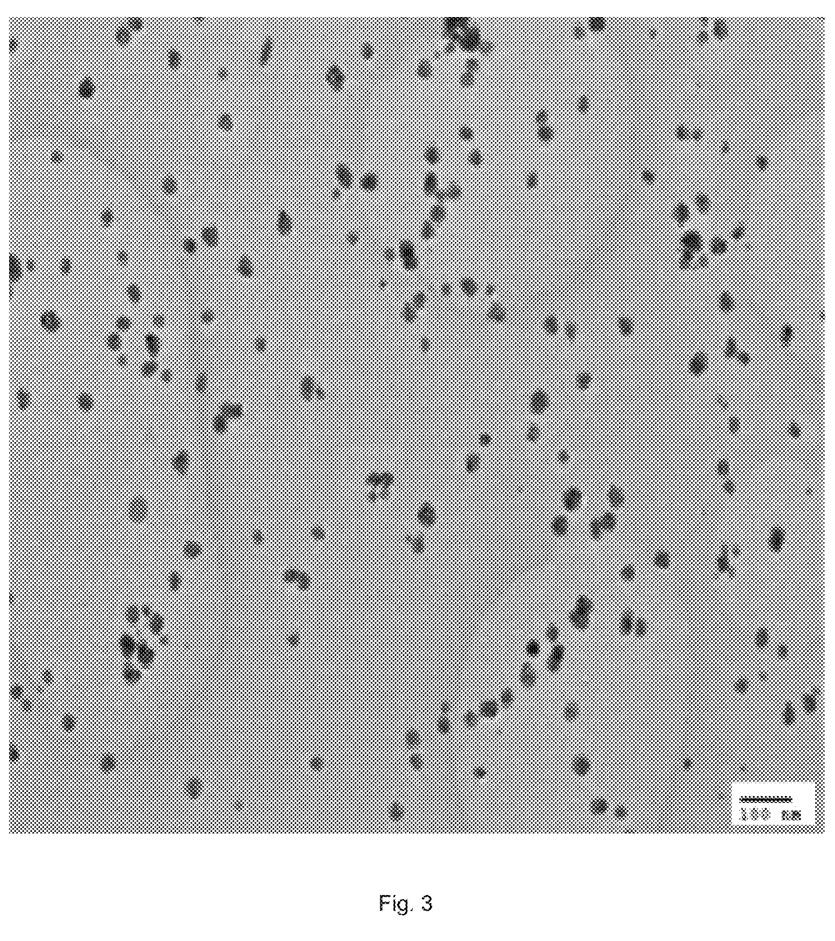
FIG. 3 is a Transmission Electron Microscopy (TEM) image of silver nanoparticles (100 ppm) prepared at 60° C. and a pH of 11.5 for 30 minutes.

1 ml of the second solution was added dropwise to the first solution at 60° C. at a pH of 11.5 under vigorous stirring for 30 minutes. During the addition of the second solution the color gradually turned from an obscure white color to transparent yellow color which indicates the formation of silver nanoparticles. The UV-Vis spectrum of the resulting solution features an absorption band around 400 nm (FIG. 1) which can be attributed to the plasmon absorption band of the synthesized silver nanoparticles. The EDX spectrum (FIG. 2) shows two peaks located between 2.5 keV and 3.5 keV which can be attributed to the prepared silver nanoparticles. Quantitative analysis of the EDX spectra proved a high silver content of about 85%. The size and the size distribution of the prepared silver nanoparticles was determined by Transmission Electron Microscopy (TEM). The mean particle size was determined with 4-8 nm (FIG. 3).

Example 4

Preparation of Silver Nanoparticles (500 ppm)

Example 4 was prepared according to Example 3 but using 5 ml of the second solution. TEM analysis indicated an increasing particle size by increasing the concentration of silver ions.

Example 5

Preparation of Silver Nanoparticles (1000 ppm)

Example 5 was prepared according to Example 3 but using 10 ml of the second solution. TEM analysis indicated an increasing particle size by increasing the concentration of silver ions.

Example 6

Preparation of Silver Nanoparticles (2000 ppm)

Figure 4:
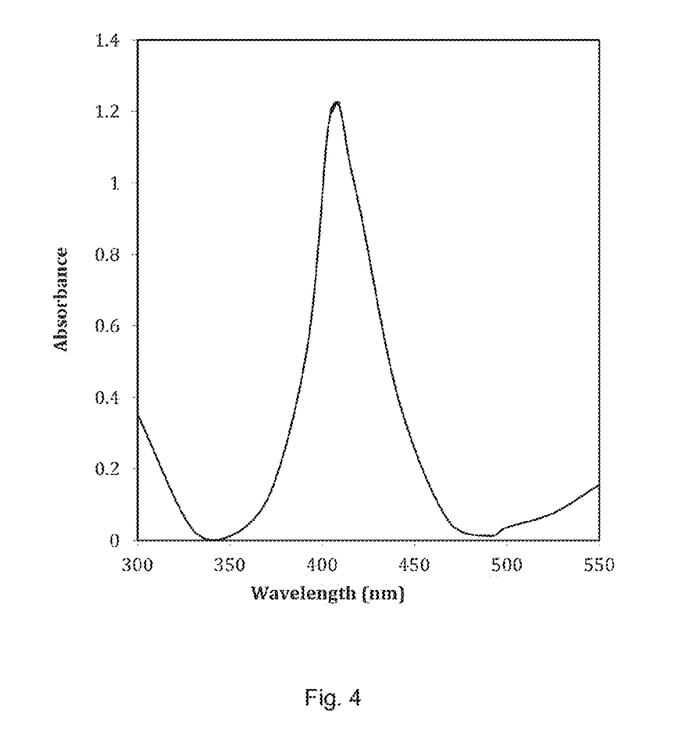
FIG. 4 is a UV-Vis absorption spectrum of silver nanoparticles (2000 ppm) prepared at 60° C. and a pH of 11.5 for 30 minutes.
Figure 5:
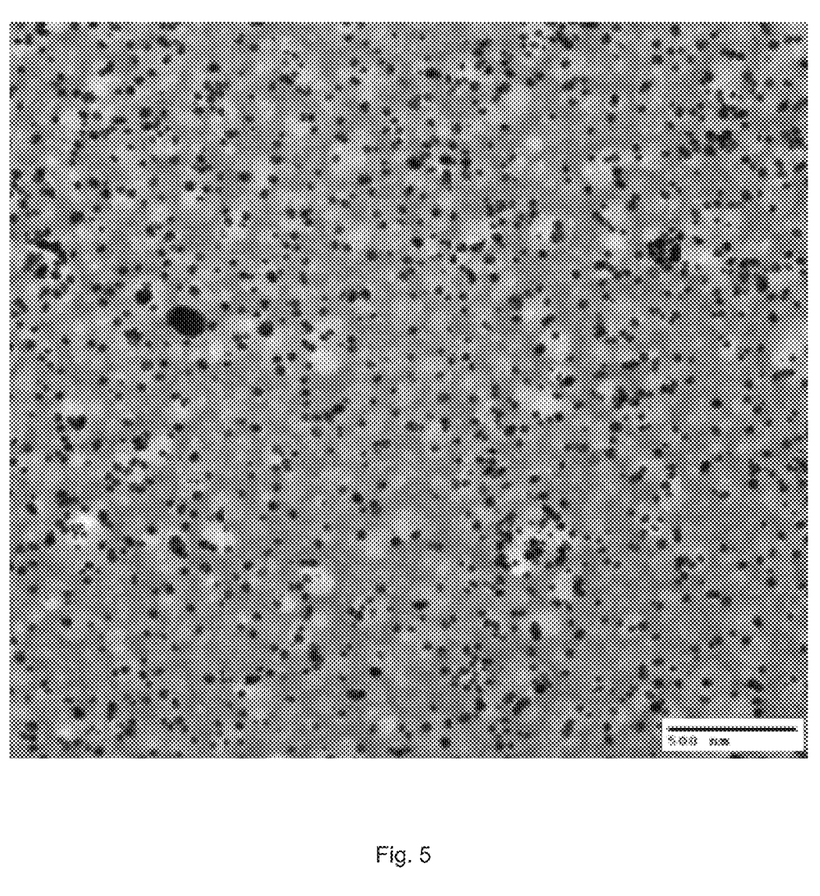
FIG. 5 is a TEM image of silver nanoparticles (2000 ppm) prepared at 60° C. and a pH of 11.5 for 30 minutes.
Figure 8:
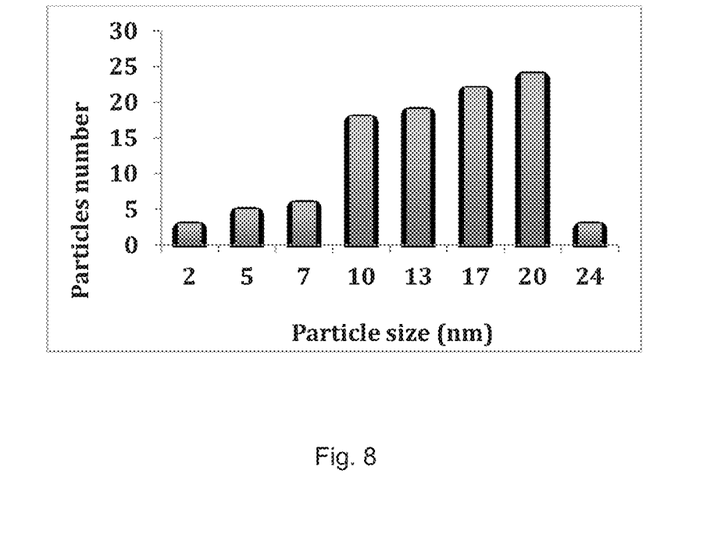
FIG. 8 is a histogram showing the particle size distribution of silver nanoparticles (2000 ppm) prepared at 60° C. and a pH of 11.5 for 30 minutes.

Example 6 was prepared according to Example 3 but using 20 ml of the second solution. By addition of the silver nitrate solution, the color gradually turned from an obscure white color to dark yellow color indicating the formation of silver nanoparticles. A shift of the plasmon band from 400 to 408 nm was observed (FIG. 4). The size of the formed silver nanoparticles increased to a range of 10-20 nm (FIG. 5). The silver nanoparticles prepared this way featured in narrow size distribution (FIG. 8).

Example 7

Long Term Stability of the Prepared Nanoparticles

Figure 6:
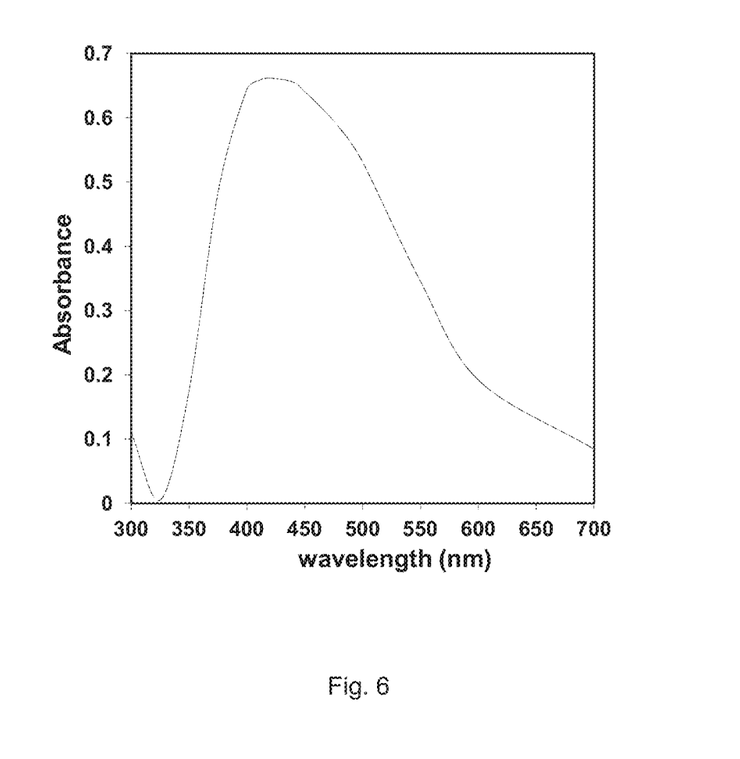
FIG. 6 is a UV-Vis absorption spectrum of silver nanoparticles (2000 ppm) prepared at 60° C. and a pH of 11.5 for 30 minutes which were stored for two years.
Figure 7:
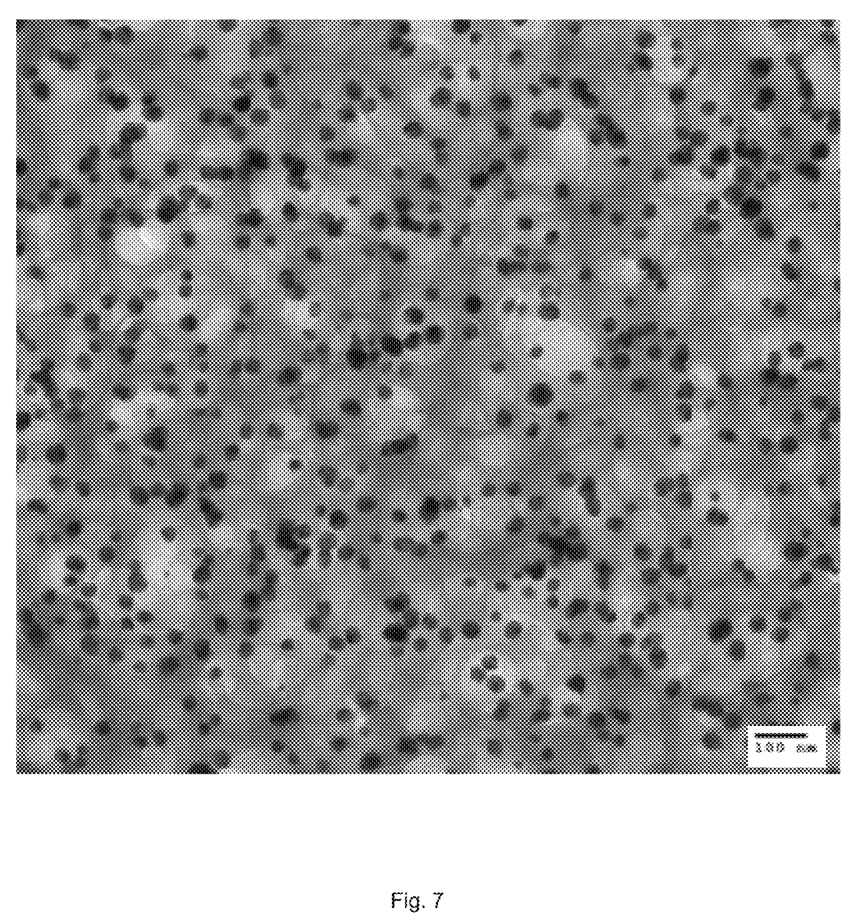
FIG. 7 is a TEM image of silver nanoparticles (2000 ppm) prepared at 60° C. and a pH of 11.5 for 30 minutes which were stored for two years.

The silver nanoparticle solution according to Example 6 was stored at room temperature over a period of two years without appreciable aggregation as monitored by UV-Vis spectroscopy (FIG. 6) and TEM (FIG. 7).

The features disclosed in the foregoing description, in the claims and drawings may both, separately and in any combination thereof, be material for realizing the invention in diverse forms.

The invention claimed is:

1. Solution comprising metal and/or metal oxide nanoparticles stabilized by an at least partially deprotonated biopolymer, wherein the biopolymer is natural starch consisting of both linear amylose and branched amylopectin, wherein the amount of amylopectin is in a range of about 70 to 80% of the starch; and concentration of the metal and/or metal oxide is in a range from 100 ppm to 2000 ppm in the composition.

2. Solution according to claim 1, wherein the diameter of the nanoparticles is in a range from 1 to 25 nm.

3. Solution according to claim 1, wherein the nanoparticles are Au, Ag, Pd, Pt, Rh, Ir, Cu, Co, Ni, Fe oxides and/or ZnO nanoparticles.

4. Solution comprising metal and/or metal oxide nanoparticles stabilized by an at least partially deprotonated biopolymer, wherein the biopolymer is natural starch consisting of both linear amylose and branched amylopectin, wherein the amount of amylopectin is in a range of about 70 to 80% of the starch; and concentration of the metal and/or metal oxide is in a range from 100 ppm to 2000 ppm in the composition, wherein the diameter of 95% of the nanoparticles is in a range from 4 to 8 nm, and the remaining 5% does not exceed 15 nm.

* * * * *